(12) United States Patent
Strom et al.

(10) Patent No.: US 7,807,359 B2
(45) Date of Patent: Oct. 5, 2010

(54) METHODS OF DETECTING TPMT MUTATIONS

(75) Inventors: Charles M. Strom, San Clemente, CA (US); Feras M. Hantash, Dana Point, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 680 days.

(21) Appl. No.: 11/566,174

(22) Filed: Dec. 1, 2006

(65) Prior Publication Data

US 2009/0117541 A1    May 7, 2009

(51) Int. Cl.
*C12Q 1/68* (2006.01)
*C12P 19/34* (2006.01)

(52) U.S. Cl. .................. 435/6; 435/91.1; 435/91.2
(58) Field of Classification Search .................. None
See application file for complete search history.

(56) References Cited

U.S. PATENT DOCUMENTS

| | | | |
|---|---|---|---|
| 5,539,517 A | 7/1996 | Cabib et al. |
| 5,790,727 A | 8/1998 | Dhadwal et al. |
| 5,846,708 A | 12/1998 | Hollis et al. |
| 5,856,095 A | 1/1999 | Evans et al. |
| 5,880,473 A | 3/1999 | Ginestet |
| 5,922,617 A | 7/1999 | Wang et al. |
| 5,943,129 A | 8/1999 | Hoyt et al. |
| 6,049,380 A | 4/2000 | Goodwin et al. |
| 6,054,279 A | 4/2000 | Nadeau et al. |
| 6,055,325 A | 4/2000 | Garini et al. |
| 6,066,459 A | 5/2000 | Garini et al. |
| 6,140,044 A | 10/2000 | Besemer et al. |
| 6,143,495 A | 11/2000 | Lizardi et al. |
| 6,191,425 B1 | 2/2001 | Imai |
| 6,252,664 B1 | 6/2001 | Barbera-Guillem |
| 6,261,776 B1 | 7/2001 | Pirrung et al. |
| 6,294,331 B1 | 9/2001 | Ried et al. |
| 2001/0007747 A1 | 7/2001 | Bochkariov et al. |
| 2001/0018514 A1 | 8/2001 | McGall et al. |
| 2004/0038269 A1 | 2/2004 | Birnboim |

FOREIGN PATENT DOCUMENTS

| | | | |
|---|---|---|---|
| WO | WO 9707201 A1 * | 2/1997 |
| WO | WO 99/60163 A | 11/1999 |
| WO | WO 00/09650 A1 | 2/2000 |
| WO | WO 00/26412 A1 | 5/2000 |
| WO | WO 00/42222 A2 | 7/2000 |
| WO | WO 00/47600 A1 | 8/2000 |
| WO | WO 01/01144 A2 | 1/2001 |
| WO | WO 01/46467 A2 | 6/2001 |
| WO | WO 02059354 A2 * | 8/2002 |
| WO | WO 02061121 A2 * | 8/2002 |
| WO | WO 03/104251 A2 | 12/2003 |

OTHER PUBLICATIONS

Fahy et al., Multiplex fluorescence-based primer extension method for quantative mutation analysis of mitrochondrial DNA and its diagnostic application for Alzheimer's disease, *Nucleic Acid Research* 25:3102-3109, 1997.
Hafner et al., Biotechniques Apr. 2001;30(4):852-6, 858, 860 passim.
Lindblad-Toh et al., Large-scale discovery and genotyping of single-nucleotide polymorphisms in the mouse. Nature Genet. Apr. 2000;24(4):381-6).
Saiki, "Amplification of Genomic DNA" in PCR Protocols, Innis et al., Eds., Academic Press, San Diego, CA 1990, pp. 13-20.

\* cited by examiner

*Primary Examiner*—Young J Kim
(74) *Attorney, Agent, or Firm*—Foley & Lardner LLP

(57) ABSTRACT

Methods and compositions are described for use in the rapid and simultaneous screening of one or more samples for one or more mutations in the TPMT gene. The methods and compositions of the present invention can be used to rapidly determine if a mutation of the TPMT gene is present in the genome of a subject. Identifying which mutations are present in an individual allows the clinician to design an appropriate therapy using drugs metabolized by TPMT for that individual.

30 Claims, 2 Drawing Sheets

```
  1 ATGGATGGTA CAAGAACTTC ACTTGACATT GAAGAGTACT CGGATACTGA GGTACAGAAA
 61 AACCAAGTAC TAACTCTGGA AGAATGGCAA GACAAGTGGG TGAACGGCAA GACTGCTTTT
121 CATCAGGAAC AAGGACATCA GCTATTAAAG AAGCATTTAG ATACTTTCCT TAAAGGCAAG
181 AGTGGACTGA GGGTATTTTT TCCTCTTTGC GGAAAAGCGG TTGAGATGAA ATGGTTTGCA
241 GACCGGGGAC ACAGTGTAGT TGGTGTGGAA ATCAGTGAAC TTGGGATACA AGAATTTTTT
301 ACAGAGCAGA ATCTTTCTTA CTCAGAAGAA CCAATCACCG AAATTCCTGG AACCAAAGTW
361 TTTAAGAGTT CTTCGGGGAA CATTTCATTG TACTGTTGCA GTATTTTTGA TCTTCCCAGG
421 ACAAATATTG GCAAATTTGA CATGATTTGG GATAGAGGAG CATTAGTTGC CATTAATCCA
481 GGTGATCGCA AATGCTATGC AGATACAATG TTTTCCCTCC TGGGAAAGAA GTTTCAGTAT
541 CTCCTGTGTG TTCTTTCTTA TGATCCAACT AAACATCCAG GTCCACCATT TTATGTTCCA
601 CATGCTGAAA TTGAAAGGTT GTTTGGTAAA ATATGCAATA TACGTTGTCT TGAGAAGGTT
661 GATGCTTTTG AAGAACGACA TAAAAGTTGG GGAATTGACT GTCTTTTTGA AAAGTTATAT
721 CTACTTACAG AAAAGTAA
```

METHODS OF DETECTING TPMT MUTATIONS

FIELD OF THE INVENTION

The invention relates to the field of diagnostic assays, in particular, assays for identifying mutations in TPMT nucleic acid.

BACKGROUND OF THE INVENTION

Thiopurine S-methyltransferase (TPMT) is a cytosolic enzyme that catalyzes metabolism of thiopurines. This metabolic pathway involving TPMT is critical for the metabolism of thiopurine-based drugs such as azathiopurine, 6-mercaptopurine, and 6-thioguanine. The level of TPMT activity varies considerably between individuals. Thus, identifying the level of TPMT activity that is present in an individual prior to thiopurine therapy can reduce or avert the onset of serious side effects.

TPMT activity exhibits genetic variation with about 89% of Caucasians and African-Americans having high TPMT activity, 11% with intermediate activity, and ~1 in 300 exhibiting TPMT deficiency. The TPMT gene is 34 kb in size and consists of 10 exons.

The wild-type allele for high enzyme activity is designated TPMT1. Four variant alleles associated with decreased enzyme activity are designated TPMT3A, TPMT3B, TPMT3C, and TPMT2. Each variant allele harbors one or two mutations. The majority of the genetic variation in TPMT activity can be attributed to three single nucleotide mutations in the TPMT gene: 1) a guanine to cytosine substitution corresponding to position 238 of the DNA coding sequence ("G238C") found in TPMT2, resulting in an amino acid change at position 80 of alanine to proline; 2) a guanine to adenine substitution corresponding to position 460 of the DNA coding sequence ("G460A") found in TPMT3B, resulting in an amino acid change at position 154 of alanine to threonine; and 3) a adenine to guanine substitution corresponding to position 719 of the DNA coding sequence ("A719G") found in TPMT3C, resulting in an amino acid change at position 240 of tyrosine to cysteine. The TPMT3A allele contains the G460A and the A719G mutations.

Methods for determining TPMT genotype have been described. See e.g., U.S. Pat. No. 5,856,095.

SUMMARY OF THE INVENTION

In a first aspect, a method is provided for determining the presence or absence of a point mutation in a TPMT gene from a sample of nucleic acids from a person by amplifying a region of the TPMT gene containing the site of the mutation to create an amplified region and performing single nucleotide primer extension to detect the identity of the nucleotide added to the extension primer, wherein the identity of the nucleotide indicates the presence or absence of a mutation in the TPMT gene. Preferred mutations include G238C, G460A, and A719G of the DNA sequence encoding TPMT (see FIG. 1; SEQ ID NO:1).

The method can be used to identify if an individual has more than one mutation in the TPMT gene. This is achieved by amplifying two or more regions the TPMT gene, wherein each amplified region contains a mutation site, and performing single nucleotide primer extension on each amplified region to detect the identity of the nucleotide added to the extension primer, wherein the identity of the nucleotide added to each primer indicates the presence or absence of a mutation in the TPMT gene. Preferred mutations to detect are in one or both TPMT alleles include G238C, G460A, and A719G.

In preferred embodiments of the above, the method for detecting mutations comprises:
a) amplifying a region of the TPMT gene containing the point mutation site to create an amplified region;
b) incubating a reaction mixture comprising:
i) the amplified region,
ii) an extension primer complementary to the amplified region, wherein the 3'-end base of the primer is positioned one base 5' to the point mutation site when the primer is hybridized to the amplified region,
iii) a DNA polymerase, and
iv) a labeled ddNTP corresponding to the nucleotide representing the mutation, under conditions wherein, in the presence of an amplified region containing the mutation, the labeled ddNTP is added to the 3'-end of the primer to generate a labeled extension primer; and
c) detecting the labeled extension primer, wherein the presence of the labeled extension primer is indicative of the presence of the mutation.

If it is desired to determine the presence of mutation at multiple TPMT sites, then step a) can include amplifying two different regions of the TPMT gene each containing the position of a point mutation site. This amplification may be done as a multiplex or may be conducted in separate vessels. Primer extension may then be conducted on each amplified region.

In still another aspect, the invention provides a method of identifying individuals who are susceptible to toxicity of thiopurine drugs due to reduced activity of TPMT by detecting the presence of one or more mutations in the TPMT gene. The detection of one or more mutations is indicative of the presence of one or more variant alleles of TPMT, which is correlated to reduced TPMT activity. In some embodiments, the method comprises amplifying a region of the TPMT gene containing the site of the mutation to create an amplified region and performing single nucleotide primer extension to detect the identity of the added nucleotide, wherein the identity of the nucleotide indicates the presence or absence of a mutation in the TPMT gene, and wherein the detection of one or more mutations is correlated with reduced TPMT activity.

This method of identifying individuals susceptible to toxicity of thiopurine drugs can include identification of more than one mutation in the TPMT gene. This is achieved by amplifying two or more regions the TPMT gene, wherein each amplified region contains a mutation site, and performing single nucleotide primer extension on each region to detect the identity of the nucleotide added to the extension primer, wherein the identity of the nucleotide added to each primer indicates the presence or absence of a mutation in the nucleic acid sample. Preferred mutations to detect are in one or both TPMT alleles include G238C, G460A, and A719G.

In some embodiments of the above approaches for identifying individuals susceptible to toxicity of thiopurine drugs aspect of the invention, the method comprises:
a) amplifying a region of the TPMT gene containing the point mutation site to create an amplified region;
b) incubating a reaction mixture comprising:
i) the amplified region,
ii) an extension primer complementary to the amplified region, wherein the 3'-end base of the primer is positioned one base 5' to the point mutation site when the primer is hybridized to the amplified region,
iii) a DNA polymerase, and
iv) a labeled ddNTP corresponding to the nucleotide representing the mutation, under conditions wherein, in the presence of an amplified region containing the mutation, the labeled ddNTP is added to the 3'-end of the primer to generate a labeled extension primer; and c) detecting the labeled extension primer, wherein the detection is indicative of the presence of the mutation in the TPMT gene of the individual, wherein the detection of one or more mutations is correlated with reduced TPMT activity.

If it is desired to determine the presence of mutation at multiple TPMT sites, then step a) can include amplifying two different regions of the TPMT gene each containing the position of a point mutation site. This amplification may be done as a multiplex or may be conducted in separate vessels. Primer extension may then be conducted on each amplified region.

As used herein, "primer extension" refers to the enzymatic addition of at least one nucleotide to the three-prime (3') hydroxy group of an extension primer, which is an oligonucleotide that is paired to a template nucleic acid (for an example of primer extension as applied to the detection of polymorphisms, see Fahy et al., Multiplex fluorescence-based primer extension method for quantitative mutation analysis of mitochondrial DNA and its diagnostic application for Alzheimer's disease, *Nucleic Acid Research* 25:3102-3109, 1997). The extension reaction is catalyzed by a DNA polymerase. Primer extension reactions can be "single base extensions" where the primer is extended by a single base. By "DNA Polymerase" is meant a DNA polymerase, or a fragment thereof, that is capable of carrying out primer extension. Thus, a DNA polymerase can be an intact DNA polymerase, a mutant DNA polymerase, an active fragment from a DNA polymerase, such as the Klenow fragment of *E. coli* DNA polymerase, and a DNA polymerase from any species including, but not limited to, thermophiles.

Addition of one or more nucleotides to the 3' end of the extension primer generates an oligonucleotide having a length greater than the extension primer. The extended oligonucleotide, therefore, has a length of at least (X+Y) nucleotides, where X is the length of the extension primer and Y is the number of bases added to the extension primer by the polymerase. If one of the nucleotides in the added sequence Y is labeled, then the extended (X+Y) oligonucleotide is labeled. In preferred embodiments, the nucleotide added is in the form of a dideoxynucleotide. Thus, extension of the primer is terminated with the addition of a single nucleotide.

In some embodiments of the above aspects of the invention, detection of the labeled extension primer further comprises capture of the extension primer on a bead (or other solid phase) and subjecting the bead to analysis, such as by flow cytometry, to detect the labeled primer bound to the bead. Preferably, the primer comprises one member of a "binding pair," which refers herein to two molecules which form a complex through a specific interaction. Thus, the extension primer can be captured on a bead through an interaction between one member of the binding pair linked to the extension primer and the other member of the binding pair coupled to the bead. In a preferred embodiment, one member of the binding pair is an oligonucleotide sequence which is part of the extension primer, and the other member of the binding pair is the complement of that binding pair oligonucleotide sequence, which is coupled to a bead. In other embodiments the binding pair is comprised of a ligand-receptor, a hormone-receptor, or an antigen-antibody.

In some embodiments of the above aspects of the invention, the added nucleotide is a labeled ddNTP. In particular embodiments, the label may be a fluorescent label (e.g., Cy5®, Cy3®, FITC, rhodamine, lanthanide phosphors, Texas red). In certain embodiments, the label may be coupled to the ddNTP through a covalent attachment. In other embodiments, a binding pair member also can be used to link the detectable label to the ddNTP. In a preferred embodiment, the binding pair is biotin and avidin or streptavidin. In this case, the ddNTP is coupled to biotin and the subsequently labeled extension primers (i.e., labeled by incorporation of biotinylated ddNTP) are detected by reacting with labeled streptavidin. In other embodiments the binding pair is comprised of a ligand-receptor, a hormone-receptor, an antigen-antibody, or an oligonucleotide-complement.

In certain embodiments, a binding pair may be employed in the capture of the extension primer on solid phase and also in the detection of the added nucleotide. In these embodiments, it is desirable that a different binding pair be used in each system (i.e., extension primer capture and detection of added nucleotide) in order to avoid competing binding between the two systems.

The skilled artisan will understand that, if one wishes to determine if a specific genotype is present in a sample, e.g., a "T" in a certain position in the TPMT sequence that would normally be a "G" in the wild-type sequence, one need only provide a single labeled ddNTP, in this case ddTTP, with an appropriate extension primer. If the "T" mutation is present, the labeled ddTTP will be incorporated into the 3' end of the extension primer. In contrast, if the wild-type nucleotide is present, no labeled extension primer will be created. Depending on the polymorphisms selected for analysis, from one to four labeled ddNTPs may be required to perform an assay. One may also choose to include all four ddNTPs or at least two relevant ddNTPs (e.g., the ddNTPs corresponding to the nucleotide in the wild-type and mutant sequences) in a reaction for convenience, or so that mutant and wild-type sequences can be labeled.

In other embodiments of the above aspects of the invention, more than one labeled ddNTP is used. In this case, the ddNTPs may be distinguishably labeled. "Distinguishably labeled," means that each type of member of a set is labeled with a label that can be distinguished from the label(s) used for other members of the set. In some aspects of the invention, the distinguishable label is a fluorescent label. For example, in a set of distinguishably labeled nucleotides (e.g., dideoxy NTPs, or ddNTPs), each type of nucleotide is labeled with a label that can be distinguished from the labels of the other types of nucleotides. Thus, for example, if four labels designated *1, *2, *3 and *4 are used to label the four types of ddNTPs, each ddATP molecule may carry label *1, each ddTTP molecule may carry label *2, each ddCTP molecule may carry label *3, and each ddGTP molecule may carry label *4. If, for example, the mutant nucleotide in a particular sequence is an adenine, when the mutation is present, only dd(T*2)TP can be added to the 3' end of the extension primer for the amplified region containing the mutation, because thymine (T) is the only base that pairs with adenine (A). The addition of the dd(T*2)TP to the 3' of the primer prevents any further primer extension because it is a dideoxynucleotide, also known as a chain-terminating nucleotide. Thus, the only primer that is 3' extended on the mutant amplified region is labeled with label *2. Detection of the signal from label *2 indicates that the mutation (i.e., adenine) is present in the sample. If the tested DNA is from an individual that is heterozygous at that position, then the signal from a second label (i.e., *1, *3 or *4) will be detected as well.

In certain embodiments of the above aspects of the invention, the presence or absence of a second mutation in a TPMT gene may be determined. Such a method further comprises amplifying a second region of a TPMT gene containing the site of the second mutation to create a second amplified region and performing single nucleotide primer extension to detect the identity of the nucleotide added to a second extension primer, wherein the identity of the nucleotide indicates the presence or absence of the second mutation.

In further embodiments of the above aspects of the invention, the presence or absence of a third mutation in a TPMT gene may be determined. Such a method further comprises amplifying a third region of a TPMT gene containing the site of the third mutation to create a third amplified region and performing single nucleotide primer extension to detect the identity of the nucleotide added to a third extension primer, wherein the identity of the nucleotide indicates the presence or absence of the third mutation.

In particular embodiments of the above aspects of the invention, the presence or absence of three mutations in a TPMT gene is determined, wherein the amplification of the regions containing the sites of the three mutations is performed in multiplex format. "Multiplex format" refers generally to the case in which two or more independent reactions occur simultaneously in a single reaction vessel. As used herein, certain steps in the methods described herein may be performed in multiplex format, including, for example, amplification or single nucleotide primer extension. Thus, as used herein a "multiplex amplification reaction" (e.g., a multiplex PCR reaction) refers to a PCR reaction where more than one primer set is included in the reaction mixture, allowing two or more different regions to be amplified by the PCR in a single reaction vessel (e.g., in a tube or in a well of a microtiter plate). By way of example, but not by way of limitation, a multiplex reaction may include a primer set capable of amplifying a region of a TPMT gene containing position 238 of SEQ ID NO:1, a primer set capable of amplifying a region of a TPMT gene containing position 460 of SEQ ID NO:1, and a primer set capable of amplifying a region of a TPMT gene containing position 719 of SEQ ID NO:1. Similarly, as used herein a "multiplex single nucleotide primer extension reaction" refers to a single nucleotide primer extension reaction where more than one extension primer is included in the reaction mixture, allowing the nucleotide at more than one mutation site or on more than one strand (i.e., sense and anti-sense strands) for a particular mutation site to be determined.

In some embodiments of the method wherein the presence or absence of two or more mutations is determined, a single region of the TPMT gene encompassing the sites of the two or more mutations is amplified. In these embodiments, it is preferred that the single nucleotide primer extension reactions corresponding to each mutation be performed in separate vessels; one vessel for each mutation. This reduces the possibility that during the detection step, a second label may be associated with an extension primer through its hybridization to the amplicon, which is hybridized to another labeled extension primer. Alternatively, the single nucleotide primer extension reaction can be performed in a multiplex format and the detection step can be adjusted by use of, for example, distinguishably labeled ddNTPs, distinguishably tagged extension primers (allowing for capture of the extension primers on distinguishably labeled beads), and multiple lasers and detectors (allowing for the simultaneous detection of multiple labels) so that the skilled artisan can determine the identity of the nucleotide added to each primer. In still other embodiments of this multiplex single nucleotide primer extension reaction, labeled extension primer can be dissociated from the amplicon (by for example, heat denaturation) following the extension reaction and separated from the amplicon by, for example, degradation of the amplicon, or blocking of the re-hybridization of the labeled extension primer to the amplicon with the addition of excess unlabeled extension primer.

In a preferred embodiment of the method wherein the presence or absence of two or more mutations is determined, a separate region of the TPMT gene is amplified for each mutation, resulting in amplified regions that contain the site of only one mutation. Preferably, the regions are amplified in multiplex format. Preferably the single nucleotide primer extension reactions are run in multiplex format.

In further embodiments of the above aspects of the invention, the single nucleotide primer extension is performed in multiplex format. In some embodiments, the single nucleotide primer extension reactions for the G238C, G460A, and A719G mutations of the TPMT gene are performed in a single vessel. In this case, the regions containing the position of each of the mutations (i.e., positions 238, 460, and 719 of SEQ ID NO:1) are amplified, preferably by multiplex PCR or are amplified individually and combined into a single reaction vessel. The multiplex single nucleotide primer extension reaction is then performed using extension primers corresponding to the site of each mutation and distinguishably labeled ddNTPs. The identity of the nucleotide added to the extension primer is then determined by detection of the label incorporated into the extension primer through the addition of a labeled ddNTP.

In preferred embodiments of the above aspects of the invention, the single nucleotide primer extension reactions corresponding to the G238C, G460A, and A719G mutations of the TPMT gene are performed in two separate reactions. In this case, the first reaction comprises labeled ddATP and extension primers to detect the presence of the G460A mutation and the absence of the A719G mutation, and the second reaction comprises labeled ddGTP and primers to detect the presence of the A719G mutation and the absence of the G238C and G460A mutations. In particular embodiments, the extension primer corresponding to the site of each mutation comprises a member of a unique binding pair. The second member of each unique binding pair is coupled to a distinguishably labeled bead. In this way each extension primer can be captured on a bead, identified, and interrogated for incorporation of labeled ddNTP. In a preferred embodiment, each extension primer comprises a distinct oligonucleotide tag, which is complementary to a oligonucleotide on a distinguishably labeled bead. Thus, following the primer extension reaction, the labeled extension primers may be captured on distinguishably labeled beads. Flow cytometry may then be used to separate beads by label and detect and identify any signal contained in the attached extension primer.

In any of the above aspects in which TPMT mutations are detected in nucleic acids from biological samples, there are embodiments in which the sample may be processed for direct use in an amplification without having to extract the nucleic acids from the sample. In these embodiments, the method further includes contacting the sample with a nucleic acid processing solution (NAPS) having a chelating agent, a denaturing agent, and a buffering agent to form a modified sample, wherein the NAPS has a pH between about 5 and about 11, and using the modified sample as a template in the amplifying step. Alternatively, the method further includes, contacting the sample with a nucleic acid processing solution (NAPS) having a chelating agent, a denaturing agent, and a buffering agent to form a modified sample, wherein the NAPS has a pH between about 5 and about 11, and wherein the modified sample provides the template nucleic acids, and amplifying the template nucleic acids, wherein the template nucleic acids have not been extracted from the modified sample.

One or more of the steps of the assays described herein, in any combination, are preferably performed in an automated fashion, typically using robotics, in order to provide for the processing of a large number of samples in a single batch run. Preferred forms of automation will provide for the preparation and separation of a plurality of labeled nucleic acids in small volumes. The term "small volumes" refers to volumes of liquids less than 2 mL, e.g., any volume from about 0.001 µL, to any volume about 2 mL, 500 µL, 200 µL, 100 µL, 10 µL, 1 µL, 0.1 µL, 0.01 µL, or 0.001 µL.

In another aspect of the invention, there are provided primers suitable for PCR amplification of portions of the TPMT gene in which contain TPMT mutations. Such primers may be designed to amplify a region encompassing a mutation by methods or software well-known in the art. Preferably primers are 10-60 nucleotides in length; preferably 10-40 nucleotides; preferably 10-30 nucleotides; or 15-25 nucleotides. Preferred primers include SEQ ID NOs:2-7.

In still another aspect of the invention there are provided extension primers that are useful for detecting the TPMT mutations. Accordingly, provided are substantially purified nucleic acids comprising 8-31 nucleotides fully complementary to a segment of the TPMT gene that is upstream of a mutation site and terminating one nucleotide 5' of that mutation site. Suitable extension primers are described herein, and may be one of the sequences set forth in SEQ ID NOs:14-21.

As used herein, the term "purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "purified" oligonucleotide is preferably at least 10% pure. A "substantially purified" oligonucleotide is preferably at least 50% pure, more preferably at least 75% pure, and most preferably at least 95% pure.

"Region" as used herein in reference to a gene, refers to a piece of contiguous nucleic acid. In certain embodiments, a region includes one or more mutation sites, preferably one or more mutation sites within the TPMT gene. In preferred embodiments a region containing one or more mutation sites is amplified. In such embodiments the region contains at least 40 nucleotides, preferably at least 50 nucleotides, preferably at least 75 nucleotides, preferably at least 100 nucleotides, preferably at least 200 nucleotides, or preferably at least 500 nucleotides. In certain embodiments, the region can be 1000, 2000, 3000, or even 5000 nucleotides, provided that the DNA strands can be separated and that the extension primer and polymerase are able to hybridize and extend. In particular examples, amplification may include amplifying portions of nucleic acids between about 30 and 50, between about 50 and 100, or between about 100 and 500 nucleotides in length or between about 500 to 1000 nucleotides in length; for example, in some embodiments, amplification products may be between about 250 to about 370 nucleotides in length. The length of the amplicon may be pre-determined by selecting the proper primer sequences.

As used herein, a "mutation" is at least a single nucleotide variation (i.e., a "point mutation") in a nucleic acid sequence relative to the normal sequence or wild-type sequence. A mutation may include a substitution, a deletion, an inversion or an insertion. With respect to an encoded polypeptide, a mutation may be "silent" and result in no change in the encoded polypeptide sequence or a mutation may result in a change in the encoded polypeptide sequence. For example, a mutation may result in a substitution in the encoded polypeptide sequence. A mutation may result in a frameshift with respect to the encoded polypeptide sequence. A "mutant" may include a nucleic acid having at least one mutation. The "mutation site" refers to the location in the nucleic acid where the mutation can be found, when present.

As used herein, the term "sample" or "test sample" refers to any liquid or solid material containing nucleic acids. In preferred embodiments, a test sample is obtained from a biological source (i.e., a "biological sample"), such as cells in culture or a tissue sample from an animal, most preferably, a human. Preferred sample tissues include, but are not limited to, blood, bone marrow, body fluids, cerebrospinal fluid, plasma, serum, or tissue (e.g. biopsy material).

As used herein, "nucleic acid" refers broadly to genomic DNA, segments of a chromosome, segments or portions of DNA, cDNA, and/or RNA. Nucleic acid may be derived or obtained from an originally isolated nucleic acid sample from any source (e.g., isolated from, purified from, amplified from, cloned from, reverse transcribed from sample DNA or RNA).

"Genomic nucleic acid" or "genomic DNA" refers to some or all of the DNA from the nucleus of a cell. Genomic DNA may be intact or fragmented (e.g., digested with restriction endonucleases by methods known in the art). In some embodiments, genomic DNA may include sequence from all or a portion of a single gene or from multiple genes, sequence from one or more chromosomes, or sequence from all chromosomes of a cell. In contrast, the term "total genomic nucleic acid" is used herein to refer to the full complement of DNA contained in the genome of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA. Genomic nucleic acid may be obtained from the nucleus of a cell, or recombinantly produced. Genomic DNA also may be transcribed from DNA or RNA isolated directly from a cell nucleus. PCR amplification also may be used. Methods of purifying DNA and/or RNA from a variety of samples are well-known in the art.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

The term "complement" as used herein means the complementary sequence to a nucleic acid according to standard Watson/Crick pairing rules. A complement sequence can also be a sequence of RNA complementary to either the sense or antisense strand of a DNA sequence, and can also be a cDNA.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplified region" or "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

In a normal diploid eukaryote, each gene has 2 loci, i.e., 1 gene copy at the same locus (position) on each chromosome of a chromosome pair. Different versions of a gene can occur at any locus, and these versions are called alleles. Each allele may be the wild-type (normal) allele or an allelic variant. Thus, two different versions of a TPMT gene may be present in any particular subject. "Allelic variant" refers to a mutation or variation in a nucleotide sequence, such as a single nucleotide polymorphism (SNP) or any other variant nucleic acid sequence or structure (e.g., duplications, deletions, inversions, insertions, translocations, etc.) in a gene encoding a gene that alters the activity and/or expression of the gene. Allelic variants may over- or under-express the polypeptide encoded by the gene, and/or may express proteins altered activities by virtue of having amino acid sequences that vary from wildtype sequence.

As used herein, the term "about" when used in reference to a numerical value, means plus or minus 10%.

The summary of the invention described above is non-limiting and other features and advantages of the invention will be apparent from the following detailed description of the invention, and from the claims.

BRIEF DESCRIPTION OF THE FIGURES

FIG. 1 represents the sequence of the DNA sequence encoding TPMT (SEQ ID NO.: 1).

FIG. 2A shows a hybridization between the amplification products of a multiplex PCR amplification of fragments containing the mutation sites at positions 238, 460, and 719 and the extension primers specific for the mutations at positions 460 and 719. Each extension primer contains a oligonucleotide tag (represented as a number). FIG. 2B shows the addition of ddNTPs, including labeled ddATP (ddATP*) and the addition of ddNTPs onto the 3' end of the extension primer. FIG. 2C shows a hybridization between of the extension primer to the bead. Differentially labeled beads contain an anti-tag sequence (or complementary sequence) to the tag sequence on the primer. FIG. 2D shows the bead hybridized to the extension primer through the hybridization between the extension primer tag sequence and the anti-tag sequence present on the surface of the bead. The beads are then subjected to analysis by flow cytometry which detects the presence of ddATP* on bead No. 2.

DETAILED DESCRIPTION OF THE INVENTION

Figure 2:
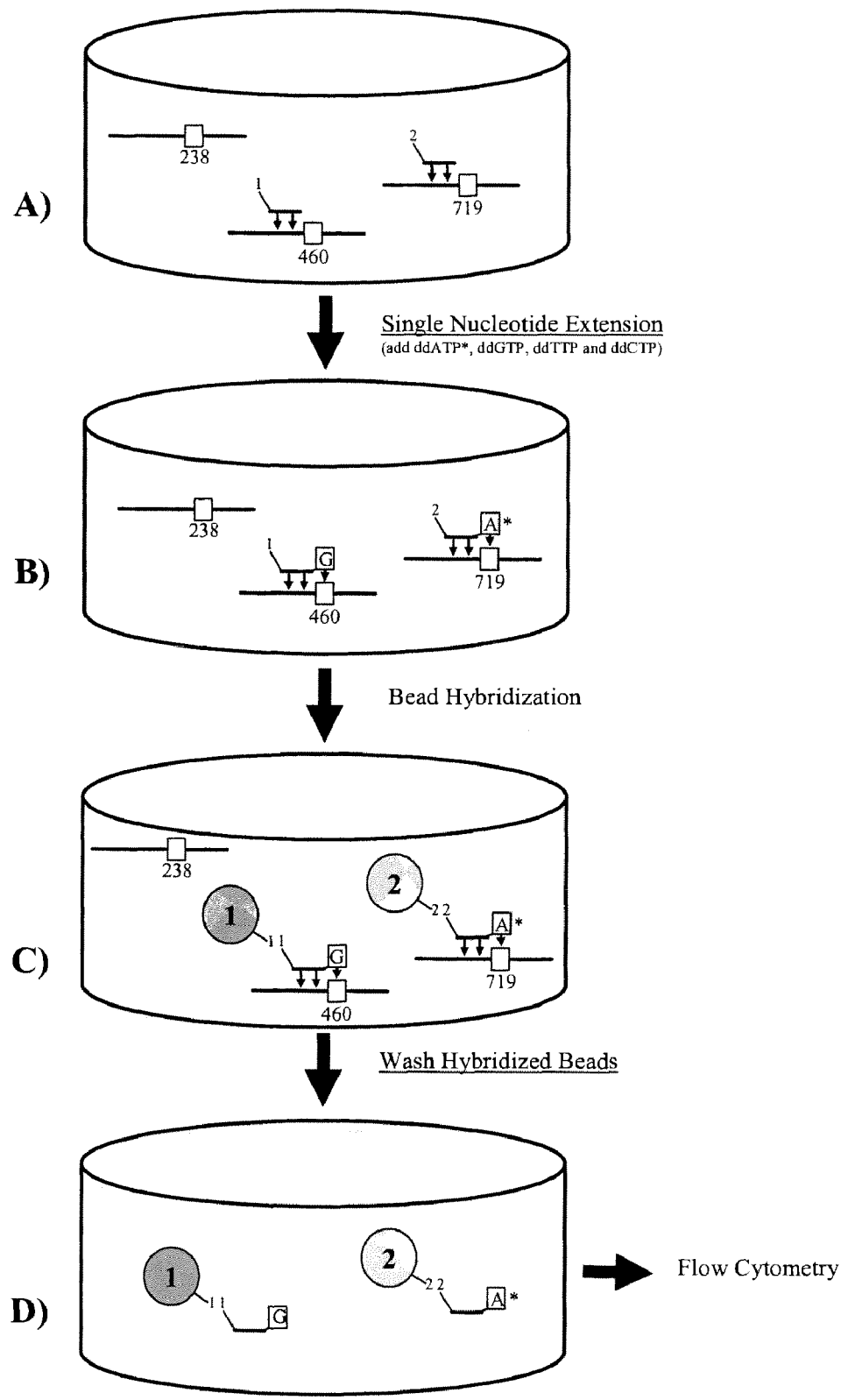
FIG. 2A-D shows an exemplary multiplex single nucleotide extension reaction in schematic form.

The invention is drawn to assays for the detection of mutations in TPMT nucleic acid. In particular, the invention provides methods for identifying individuals harboring TPMT mutations that affect metabolism of thiopurines or other drugs or compounds metabolized by TPMT.

Reagents

Amplification Primers

Genomic DNA or cDNA may be subject to amplification by the polymerase chain reaction or related methods using primers directed to specific portions of the TPMT gene which contain a mutation to be detected. In preferred embodiments, genomic DNA is amplified.

Primers may be designed to amplify a region encompassing a mutation by methods or software well-known in the art. Preferably primers are 10-60 nucleotides in length; preferably 10-40 nucleotides; preferably 10-30 nucleotides; or 15-25 nucleotides.

Provided herein are the sequences of primers suitable for PCR amplification of portions of the TPMT gene in which contain TPMT mutations, using genomic DNA as the template (see, for example, Table 1 below).

TABLE 1

Exemplary amplification primers

| Primer Location in TPMT Gene | Primer Name | Primer Sequence | Position in GenBank Accession No. AB045146 |
|---|---|---|---|
| Exon 5 | TPMT-E5F | 5'-TCTTTGAAACCCTATGAACCTG-3' (SEQ ID NO: 2) | 12089-12110 |
| Intron 5 | TPMT-5R | 5'-TAGGAACCATCGGACACATG-3' (SEQ ID NO: 3) | 12435-12454 |

TABLE 1-continued

Exemplary amplification primers

| Primer Location in TPMT Gene | Primer Name | Primer Sequence | Position in GenBank Accession No. AB045146 |
|---|---|---|---|
| Intron 6 | TPMT-16F | 5'-CTCCACACCCAGGTCCACACATT-3' (SEQ ID NO: 4) | 16753-16775 |
| Intron 7 | TPMT-17R | 5'-GTATAGTATACTAAAAAATTAAGACAGCTAAAC-3' (SEQ ID NO: 5) | 17010-17042 |
| Intron 9 | TPMT-19F | 5'-AATCCCTGATGTCATTCTTCATAGTATTT-3' (SEQ ID NO: 6) | 25122-25150 |
| Exon 10 | TPMT-R971 | 5'-CATCCATTACATTTTCAGGCTTTAGCATAAT-3' (SEQ ID NO: 7) | 25342-25372 |

In addition to the sequence that ensures hybridization to the target site, an amplification primer may have additional nucleotides added to the 5' end that need not participate in specific binding to the TPMT sequence. Thus, such primers may extend for 15 to 75 nucleotides in length, preferably 17 to 50 nucleotides in length, and more preferably from 20 to 30 nucleotides in length, beyond the TPMT sequence. In some embodiments, the additional 5' sequence may include a universal linker sequence that acts to stabilize the products during PCR. Exemplary amplification primers containing a universal linker sequence are shown in Table 2 below universal linker portion of each primer shown in bold.

Exemplary oligonucleotides that may be used as primers to amplify a region of the TPMT gene containing the mutation site at position 238 of the coding sequence include 5'-GCG-GTCCCAAAAGGGTCAGT-TGTCTTTGAAACCCTATGAACCTG-3' (SEQ ID NO:8) and 5'GCGGTCCCAAAAGGGTCAGTTGTAG-GAACCATCGGACACATG-3' (SEQ ID NO:9). These primers amplify a fragment of exon 5 and intron 5 of 366 base pairs, resulting in an amplification product of 410 base pairs (the additional length is provided by the linker sequence contained in the primers).

TABLE 2

Exemplary amplification primers containing a universal linker sequence

| Primer Location in TPMT Gene | Primer Name | Primer Sequence | Position in GenBank Accession No. AB045146 |
|---|---|---|---|
| Exon 5 | TPMT-E5F-Linker | 5'GCGGTCCCAAAAGGGTCAGTTGTCTTTGAAACCCTATGAACCTG-3' (SEQ ID NO: 8) | 12089-12110 |
| Intron 5 | TPMT-5R-Linker | 5'GCGGTCCCAAAAGGGTCAGTTGTAGGAACCATCGGACACATG-3' (SEQ ID NO: 9) | 12435-12454 |
| Intron 6 | TPMT-16F-Linker | 5'GCGGTCCCAAAAGGGTCAGTTGCTCCACACCCAGGTCCACACATT-3' (SEQ ID NO: 10) | 16753-16775 |
| Intron 7 | TPMT-17R-Linker | 5'GCGGTCCCAAAAGGGTCAGTTGGTATAGTATACTAAAAAATTAAGACAGCTAAAC-3' (SEQ ID NO: 11) | 17010-17042 |
| Intron 9 | TPMT-19F-Linker | 5'GCGGTCCCAAAAGGGTCAGTTGAATCCCTGATGTCATTCTTCATAGTATTT-3' (SEQ ID NO: 12) | 25122-25150 |
| Exon 10 | TPMT-R971-Linker | 5'GCGGTCCCAAAAGGGTCAGTTGCATCCATTACATTTTCAGGCTTTAGCATAAT-3' (SEQ ID NO: 13) | 25342-25372 |

Exemplary oligonucleotides that may be used as primers to amplify a region of the TPMT gene containing the mutation site at position 460 of the coding sequence include 5'-GCG-GTCCCAAAAGGGTCAGTTGCTCCACACCCAGGT CCACACATT-3' (SEQ ID NO:10) and 5'-GCGGTC-CCAAAAGGGTCAGTTGGTATAGTATAC-TAAAAAATTAAGACAGCT AAAC-3' (SEQ ID NO:11). These primers amplify a fragment of intron 6, exon 7, and intron 7 of 290 base pairs, resulting in an amplification product of 334 base pairs (the additional length is provided by the linker sequence contained in the primers).

Exemplary oligonucleotides that may be used as primers to amplify a region of the TPMT gene containing the mutation site at position 719 of the coding sequence include 5'GCG-GTCCCAAAAGGGTCAGTTGAATCCCT-GATGTCATTCTTCATAGTATTT-3' (SEQ ID NO:12) and 5'-GCGGTCCCAAAAGGGTCAGTTGCATC-CATTACATTTTCAGGCT TTAGCATAAT-3' (SEQ ID NO:13). These primers amplify a fragment of intron 9 and exon 10 of 251 base pairs, resulting in an amplification product of 295 base pairs (the additional length is provided by the linker sequence contained in the primers).

Extension Primers

The present invention also provides extension primers that are useful for detecting the TPMT mutations. Accordingly, provided are substantially purified nucleic acids comprising 8-35 nucleotides fully complementary to a segment of the TPMT gene that is upstream of a mutation site and terminating one nucleotide 5' of that mutation site. Preferred TPMT extension primers may be labeled with a tag or member of a binding pair to enable the capture of the extension primer on solid phase. Exemplary extension primers are provided in Table 3 below.

primer could be designed to be either the sense or anti-sense strand of DNA; in either case, the extension primer would be designed so that when that primer is extended through incorporation of a nucleotide, the nucleotide incorporated corresponds to the mutation site. Extension primers should be of a length sufficient to provide specific hybridization to the target sequence of interest. Such primers preferably comprise an exact complement to the sequence of interest for 15 to 75 nucleotides in length, preferably 17 to 50 nucleotides in length, and more preferably from 20 to 30 nucleotides in length. The extension primer sequence has a 3 terminus that pairs with a nucleotide base that is, in the sample nucleic acid to which the primer is hybridized, one base 5' to the mutation site. Suitable extension primers are described herein, and may be one of the sequences set forth in SEQ ID NOs:14-21.

In addition to the sequence that ensures hybridization to the target site, an extension primer may have additional nucleotides added to the 5' end that need not participate in specific binding to the TPMT sequence. Thus, such primers may extend for 15 to 75 nucleotides in length, preferably 17 to 50 nucleotides in length, and more preferably from 20 to 30 nucleotides in length, beyond the TPMT sequence. In some embodiments, the additional 5' sequence may include a member of a binding pair such as an oligonucleotide tag. Such an oligonucleotide tag may be complementary an oligonucleotide conjugated to the surface of a bead. In this embodiment, the extension primer may be captured by hybridization of the oligonucleotide tag on the extension primer to the comple-

TABLE 3

Exemplary extension primers

| Mutation | Primer name | Primer Sequence | Position in GenBank Accession No. AB045146 |
|---|---|---|---|
| G238C Sense strand | 2AF | 5'TAAGTGTAAATGTATGATTTTATGCAG GTTT-3' (SEQ ID NO: 14) | 12194-12224 |
| G238C Antisense strand | 2AR | 5'AACTACACTGTGTCCCCGGTCTG-3' (SEQ ID NO: 15) | 12226-12248 |
| G460A | 3A1F | 5'AATTTGACATGATTTGGGATAGA GGA-3' (SEQ ID NO: 16) | 16928-16953 |
| A719G | 3A2F | 5'GGGAATTGACTGTCTTTTTGAAAAGTT AT-3' (SEQ ID NO: 17) | 25241-25269 |

Preferably, an extension primer has a nucleotide sequence that hybridizes in a complementary fashion to a portion of the TPMT gene immediately upstream of a mutation such that the hybridized extension primer terminates one nucleotide 5' to the mutation site. Accordingly, extension of that primer by one base will incorporate the nucleotide in the mutation site. One of skill in the art would recognize that the extension mentary oligonucleotide on the bead. Thus, following the incorporation of a labeled ddNTP into an extension primer, the labeled extension primers may be captured and the signal detected, such as by flow cytometry. Exemplary extension primers comprising an oligonucleotide tag are provided in Table 3 below with the oligonucleotide tag portion of the primer shown in bold.

TABLE 4

Exemplary extension primers containing an oligonucleotide tag

| Mutation | Primer name | Primer Sequence | Position in GenBank Accession No. AB045146 |
|---|---|---|---|
| G238C Sense strand | 2AF Tag | 5'TTCACTTTTCAATCAACTTAAGTGTA AATGTATGATTTTATGCAGGTTT-3' (SEQ ID NO: 18) | 12194-12224 |
| G238C Antisense strand | 2AR Tag | 5'CTTTTCATCAATAATCTTACCTTTAA CTACACTGTGTCCCCGGTCTG-3' (SEQ ID NO: 19) | 12226-12248 |
| G460A | 3A1F Tag | 5'TACACTTTAAACTTACTACACTAAA ATTTGACATGATTTGGGATAGAGGA-3' (SEQ ID NO: 20) | 16928-16953 |
| A719G | 3A2F Tag | 5'TACACTTTCTTTCTTTCTTTCTTTGG GAATTGACTGTCTTTTTGAAAAGTTAT-3' (SEQ ID NO: 21) | 25241-25269 |

Sample Preparation

The methods of the present invention can be used to detect the presence of mutations in TPMT nucleic acid. Preferred nucleic acid for use in invention methods is genomic DNA, however cDNA or mRNA can also be used to detect mutations within the coding region of the TPMT gene. Therefore, the methods may be performed using any biological sample containing TPMT nucleic acid. Preferred biological samples include any genomic DNA-containing body fluid (e.g., blood) or tissue sample from an individual.

Methods of obtaining test samples are well-known to those of skill in the art and include, but are not limited to, aspirations, drawing of blood or other fluids, swabbing of tissues, and the like. The test sample may be obtained from an individual or patient. The test sample may contain cells or fluid obtained from a patient undergoing treatment with a thiopurine drug. The test sample may be a cell-containing liquid or a tissue or an acellular body fluid (e.g., plasma or serum). Samples may include, but are not limited to, whole blood, serum, plasma, saliva, cerebrospinal fluid (CSF), pericardial fluid, pleural fluid, urine, and eye fluid. Samples may also be processed, such as fractionation, purification, or cellular organelle separation.

Nucleic acids, including the TPMT sequence of interest, may be isolated from biological samples through the use of routine methods (see, for example Diagnostic Molecular Microbiology: Principles and Applications (Persing et al. (eds), 1993, American Society for Microbiology, Washington D.C.)). Various commercial nucleic acid purification kits, such as QIAGEN® BioRobot™ and MagNA Pure LC DNA Isolation Kit are known to the skilled artisan, and used to isolate nucleic acids.

In other embodiments, a biological sample may be processed for direct use in nucleic acid amplification reactions without extracting the nucleic acids from the rest of the sample. In these embodiments, the sample is contacted with a "nucleic acid processing solution" (NAPS) to form a modified sample, which can be used directly as template in an amplification reaction. In preferred embodiments, the biological sample is a cell sample or an acellular body fluid sample.

In particular embodiments, the NAPS has a pH from about 5.0 and about 11.0, preferably about 6.0 to about 11.0, preferably 7.5 to about 10.0, and more preferably about 7.0. In embodiments wherein DNA is the template for direct PCR, a pH from about 7.0 to about 10.0, or about 7.5, about 8.0, or about 8.0 to about 9.0 can be used. In embodiments wherein RNA is the template for direct or indirect PCR (e.g., RT-PCR), a pH from about 5.0 to about 7.0, desirably from about 6.5 to about 6.8 can be used. A buffer can be added to the NAPS to maintain the pH in a constant range. Such buffers are well-known in the art and include HEPES, TRIS, carbonate buffer, or BES.

The NAPS includes one or more chelating agents to form complexes with metal ions. Without wishing to be bound thus, it is believed that the chelating agent prevents metal ions from binding to DNA, removes metal ions that have already bound to DNA, or bind to metal ions (e.g., Fe(II)/Fe(III) or Cu(I)/Cu(II)) strongly enough to inhibit their redox cycling, and hence, the formation of reactive oxygen species. The chelating agent can be selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetet-raacetic acid (TETA), and desferrioximine, or chelator analogs thereof. Desirably, the chelating agent is cyclohexane diaminetetraacetate (CDTA), diethylenetriamine pentaacetic acid (DTPA), tetraazacyclododecanetetraace-tic acid (DOTA), and desferrioximine, and most desirably, the chelating agent is cyclohexane diaminetetraacetate (CDTA). Stronger chelators (i.e., chelators with a higher dissociation constant than EDTA when bound to a metal) include, but are not limited to, CDTA, DTPA, DOTA, TETA, and desferrioximine, or chelator analogs thereof may be used in the NAPS as the only chelating agent or may be used in combination with another chelating agent. The amount or concentration of the chelating agent will depend upon its affinity for metal, which may need to be determined empirically. For CDTA, concentrations in the 1-20 mM range are sufficient, however other concentrations would work.

The NAPS includes one or more denaturing agents such as a detergent, chaotrope, or alcohol. Preferred denaturing agents can be selected from the group consisting of: urea, sodium dodecyl sulfate, dodecyl sulfate, guanidinium chloride, guanidinium thiocyanate, perchlorate, and an alcohol. Preferably, the denaturing agent is urea, dodecyl sulfate, or an alcohol, wherein the alcohol is 10%, 20%, 30%, 40%, 50%, or even 60% of the total NAPS volume. Suitable alcohols include methanol, ethanol, n-propanol, isopropanol, n-butanol, trifluoroethanol, phenol, or 2,6-di-tert-butyl-4-methylphenol.

In certain embodiments, the NAPS further comprises one or more reducing agents. Suitable reducing agents include ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof. Preferably, the reducing agent is ascorbic acid, erythiorbate, N-acetylcysteine, dithiothreitol, or 2-mercaptoethanol, and more preferably, the reducing agent is ascorbic acid or 2-mercaptoethanol. In particular embodiments, the concentration of the reducing agent in the NAPS is greater than or equal to 50 millimolar. Antioxidant free-radical scavengers are also useful as reducing agents. Examples include antioxidant vitamins, antioxidant hormones, antioxidant enzymes, thiols, and phenols.

In some embodiments, the NAPS may further comprise an antimicrobial agent. "Antimicrobial agent" as used herein refers to a substance that reduces the rate of growth of a microbial organism compared to the rate of growth of the microbe in the absence of that substance. A reduction in the rate of growth of a microbe may be by at least 5%, preferably, by at least 10%, more preferably, by at least 20%, at least 50%, or at least 75%, and most preferably, by 90% or more. Antimicrobial agent includes substances that affect the viability, virulence, or pathogenicity of a microbe. An antimicrobial agent can be naturally occurring (e.g., derived or obtained from bacteria), synthetic, or recombinant. An antimicrobial agent may have static, cidal, or both properties. An antimicrobial agent is static if it inhibits cell division without affecting the viability of the inhibited cell. An antimicrobial agent is cidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is static at a given concentration may be cidal at a higher concentration. Certain static substances are not cidal at any concentration. Preferably, the solution includes an alcohol as an antimicrobial agent, preferably ethanol.

In still other embodiments, the NAPS further includes a ribonuclease inhibitor. Preferred ribonuclease inhibitors are selected from the group consisting of: heparin, heparan sulfate, oligo(vinylsulfonic acid), poly(vinylsulfonic acid), oligo(vinylphosphonic acid), and poly(vinylsulfuric acid), or salts thereof. The inclusion a ribonuclease inhibitor in the solution is particularly preferred when template nucleic acid in the sample is to be RNA, particularly mRNA, or when the template nucleic acid is from a microbe.

As used herein, the term "biological sample" refers to any liquid or solid material that is obtained from a biological source, preferably from an animal, most preferably from a human. A biological sample may be a cell sample or may be an acellular liquid sample. In preferred embodiments, the acellular liquid sample is an acellular body fluid sample.

As used herein, the term "cell sample" includes any source of cells containing nucleic acids that are desired to be used as a template in a nucleic acid amplification reaction. Cells may be prokaryotic or eukaryotic. Eukaryotic cell samples may be animal or plant cells. Preferred eukaryotic cell samples are mammalian cells, preferably human. In some embodiments, a cell sample can be cells in culture or a tissue sample from an animal, most preferably, a human. Tissue samples include, but are not limited to, blood, bone marrow, cell-containing body fluids such as cerebrospinal fluid, or tissue (e.g., biopsy material). Preferred samples include whole blood or white blood cells (WBC). Cell samples may be packed cells or cells suspended in liquid.

The terms "body fluid" or "bodily fluid" are used interchangeably herein and refer to a fluid sample from a human or other animal. Body fluids include, but are not limited to, amniotic fluid, blood, cerebrospinal fluid, peritoneal fluid, plasma, pleural fluid, saliva, semen, serum, sputum, tears, and urine. Body fluids may be cell-containing or may be acellular.

As used herein "acellular body fluid" refers to a body fluid lacking cells. Such acellular body fluids are generally produced by processing a cell-containing body fluid by, for example, centrifugation or filtration, to remove the cells. Acellular body fluid, however, may contain cell fragments or cellular debris. Preferred acellular body fluids are plasma and serum.

As used herein "modified biological sample" or "modified sample" are used interchangeably and refers to a biological sample that has been processed so that the nucleic acids contained therein may be directly amplified by a standard nucleic acid amplification method. Nucleic acids in a modified biological sample need not be extracted from the sample. Preferably, modified biological samples are the result of contacting a biological sample with a NAPS comprising a chelating agent, a denaturing agent, and a buffering agent, as described herein Modified samples include modified cell samples and modified acellular body fluid samples.

As used herein "modified cell sample" refers to a cell sample that has been processed so that the nucleic acids contained therein may be directly amplified by a standard nucleic acid amplification method. Nucleic acids in a modified cell sample need not be extracted from the sample. Preferably, modified cell samples are the result of contacting a cell sample with a NAPS comprising a chelating agent, a denaturing agent, and a buffering agent, as described herein.

As used herein "modified acellular body fluid sample" refers to an acellular body fluid sample that has been processed so that the nucleic acids contained therein may be directly amplified by a standard nucleic acid amplification method. Nucleic acids in a modified acellular body fluid sample need not be extracted from the sample. Preferably, modified acellular body fluid samples are the result of contacting an acellular body fluid sample with a NAPS comprising a chelating agent, a denaturing agent, and a buffering agent, as described herein.

As used herein the term "extracted" used in reference to nucleic acids in a cell sample means that the nucleic acids have been physically separated from cells containing the nucleic acid by addition of a sufficient volume of organic solvent to lyse the cells and separate the protein from the nucleic acids, wherein the nucleic acid in the aqueous phase is separated from the protein. The nucleic acids in the aqueous phase can be concentrated by addition of a sufficient volume of ethanol to precipitate the nucleic acids. Other methods of extracting nucleic acids include the capture of nucleic acids on solid phase using, for example, an oligonucleotide-coupled bead (e.g., oligo-dT). When used in reference to nucleic acids in an acellular body fluid, extracted means that the nucleic acids have not been separated from the sample by, for example, alcohol precipitation.

In some embodiments, the method may include a centrifugation step. For example, a centrifugation step may be used to concentrate the cells of the cell sample prior to the addition of NAPS. In another example, a centrifugation step may be used to remove cellular debris from a modified cell sample. Such a centrifugation step is not considered an extraction of nucleic acids.

As used herein, the phrase "using the modified cell sample as a template in a nucleic acid amplification reaction" means that the nucleic acids have not been extracted from the modified cell sample prior to amplifying the template nucleic acids contained therein. Similarly, the phrase "using the modified acellular body fluid sample as a template in a nucleic acid amplification reaction" means that the nucleic acids have not been extracted from the modified acellular body fluid sample prior to amplifying the template nucleic acids contained therein.

In some embodiments, NAPS may be added directly to cell samples or may be added to packed cells obtained from cell samples in which the cells have been pelleted by centrifugation. NAPS is added to the cell sample at a ratio of, for example, 1:1, 1:2, 1:3, 1:4, 1:5 or higher of cell sample to NAPS. The actual ratio depends on the cell concentration. In preferred embodiments, the cell sample is whole blood and is mixed with NAPS at a ratio of, for example, 1:1, 1:2, 1:3, 1:4, 1:5, or higher of blood to NAPS. Cell samples in which the cells have been concentrated and thus have a higher density of cells (e.g., a packed cell sample) may require more NAPS than those cell samples in which the cells have not been concentrated. For example, in processing a sample of packed cells, a volume of NAPS equivalent to 2-3 times (or higher) the volume of the packed cells may be used.

In one example, a NAPS of 2% SDS, 10 mM EDTA, and 50 mM Tris-HCl pH 8.0 is added to a sample of blood to prepare the sample for direct use in PCR. In another example, a NAPS of 0.5M NaOAc, 0.2M Tris-HCl, 0.15M sodium ascorbate, 10 mM CDTA, 1% SDS, 30% (v/v) ethanol, pH 9.5 (see PCT International Publication No. WO03104251 at Table 3, lane 1) is added to a sample of blood to prepare the sample for direct use in PCR. In a further example, the NAPS can be the DNA preserving solution contained in the Oragene™ DNA Self-Collection Kit (DNA Genotek, Ottawa, Ontario, Canada). In this case, a blood sample is applied to the sample reservoir, the reservoir is capped, releasing the DNA preserving solution into the chamber containing the blood, thus stabilizing the DNA that is present. The composition of additional NAPS are described in PCT International Publication No. WO03104251 or U.S. Patent Application Publication No. 2003-104251 (see "compositions", at, for example, Table 3).

In other embodiments, NAPS may be added directly to acellular body fluid samples. NAPS is added to the acellular body fluid sample at a ratio of, for example, 1:1, 1:2, 1:3, 1:4, 1:5 or higher of acellular body fluid sample to NAPS. The actual ratio may depend on the type of acellular body fluid and the concentration of nucleic acids contained therein. In preferred embodiments, the acellular body fluid sample is plasma and is mixed with NAPS at a ratio of, for example, 1:1, 1:2, 1:3, 1:4, 1:5, or higher of plasma to NAPS.

In one example, a NAPS of 2% SDS, 10 mM EDTA, and 50 mM Tris-HCl pH 8.0 is added to a sample of plasma to prepare the sample for direct use in PCR. In another example, a NAPS of 0.5M NaOAc, 0.2M Tris-HCl, 0.15M sodium ascorbate, 10 mM CDTA, 1% SDS, 30% (v/v) ethanol, pH 9.5 (see PCT International Publication No. WO03104251 at Table 3, lane 1) is added to a sample of plasma to prepare the sample for direct use in PCR. In a further example, the NAPS can be the DNA preserving solution contained in the Oragene™ DNA Self-Collection Kit (DNA Genotek, Ottawa, Ontario, Canada). In this case, a plasma sample is applied to the sample reservoir, the reservoir is capped, releasing the DNA preserving solution into the chamber containing the plasma, thus stabilizing the DNA that is present. The composition of additional NAPS are described in PCT International Publication No. WO03104251 or U.S. Patent Application Publication No. 2003-104251 (see "compositions", at, for example, Table 3).

Following addition of the NAPS, the resulting modified sample may be further treated with an optional Purifier solution (DNA Genotek, Ottawa, Ontario, Canada).

The modified sample may be optionally centrifuged and the supernatant used as template in amplification methods.

The modified samples processed as described above may desirably be diluted in water or an appropriate buffer for optimal use as a template in an amplification reaction. The skilled artisan will recognize that the dilution factor may vary with sample type and amplification method. For example, undiluted modified samples may be too concentrated for optimal amplification of nucleic acid. Similarly, modified samples that are highly diluted may have too low of a concentration of template for optimal amplification. Preferred dilutions include, but are not limited to, ratios of 1:5, 1:10, 1:25, 1:50, 1:100, 1:125, or higher of sample to water or dilution buffer. The skilled artisan will further understand that a minimal amount of testing may be needed to determine the optimal dilution factor for the specific sample used.

Amplification of TPMT Nucleic Acid

The methods described herein are discussed in reference to polymerase chain reaction ("PCR") amplification of genomic sequences. The skilled artisan will understand that numerous methods are known in the art for amplification of nucleic acids, and that these methods may be used either in place of, or together with, the disclosed PCR method. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 June 1; 29(11):E54-E54; Hafner et al., Biotechniques 2001 April; 30(4):852-6, 858, 860 passim; Zhong et al., Biotechniques 2001 April; 30(4):852-6, 858, 860 passim.

In various embodiments, TPMT gene sequences are amplified, preferably using PCR, prior to analysis by primer extension methods. Amplification primer sequences may comprise a 3' end that ensures hybridization to the target site, and may also include additional nucleotides added to the 5' end that need not participate in specific binding. Thus, such amplification primers may extend for 15 to 75 nucleotides in length, preferably 17 to 50 nucleotides in length, and more preferably from 20 to 30 nucleotides in length, only a subset of which is an exact complement to the target sequence of interest. In these embodiments, the exact complement may extend for at least 15 nucleotides, more preferably for at least 17 nucleotides, and most preferably for at least 20 nucleotides to ensure specific hybridization of the amplification primer.

Suitable forward and reverse primer sequences should flank the polymorphism region of interest. Exemplary primers for three regions of the TPMT gene are as follows:

TABLE 5

Exemplary amplification primers

| Primer Location in TPMT Gene | Primer Name | Primer Sequence |
|---|---|---|
| Exon 5 | TPMT-E5F-Linker | 5'GCGGTCCCAAAAGGGTCAGTTGTCTTTG AAACCCTATGAACCTG-3' (SEQ ID NO: 8) |
| Intron 5 | TPMT-5R-Linker | 5'GCGGTCCCAAAAGGGTCAGTTGTAGGAA CCATCGGACACATG-3' (SEQ ID NO: 9) |
| Intron 6 | TPMT-16F-Linker | 5'GCGGTCCCAAAAGGGTCAGTTGCTCCAC ACCCAGGTCCACACATT-3' (SEQ ID NO: 10) |
| Intron 7 | TPMT-17R-Linker | 5'GCGGTCCCAAAAGGGTCAGTTGGTATAG TATACTAAAAAATTAAGACAGCTAAAC-3' (SEQ ID NO: 11) |
| Intron 9 | TPMT-19F-Linker | 5'GCGGTCCCAAAAGGGTCAGTTGAATCCC TGATGTCATTCTTCATAGTATTT-3' (SEQ ID NO: 12) |
| Exon 10 | TPMT-R971-Linker | 5'-GCGGTCCCAAAAGGGTCAGTTGCATCCA TTACATTTTCAGGCTTTAGCATAAT-3' (SEQ ID NO: 13) |

In some embodiments, more than one region containing a mutation site is amplified simultaneously in the same reaction vessel using multiplex PCR. In a preferred embodiment, multiplex PCR is performed to amplify three portions of the TPMT gene. The multiplex PCR reaction generates three different amplicons: the first amplicon corresponds to exon 5 and includes nucleotide position 238; the second amplicon corresponds to exon 7 and includes nucleotide position 460; and the third amplicon corresponds to exon 10 and includes nucleotide position 719.

Once amplified, the PCR products are treated, e.g., with shrimp alkaline phosphatase (SAP) and exonuclease I, to remove excess dNTPs and PCR primers, respectively, prior to single nucleotide primer extension.

Single Nucleotide Primer Extension

As discussed herein, an amount of nucleic acid sufficient for primer extension can, but need not be, prepared by amplification, e.g., via PCR using amplification primers. As a non-limiting example, appropriate amplification primers include, but are not limited to, those having sequences set forth in SEQ ID NOS:2-13.

Amplification is followed by single nucleotide primer extension (Lindblad-Toh et al., Large-scale discovery and genotyping of single-nucleotide polymorphisms in the mouse. Nature Genet. 2000 April; 24(4):381-6). In this reaction, an oligonucleotide primer is designed to have a 3' end that is one nucleotide 5' to a specific mutation site. In some embodiments, the extension primers are labeled with a tag or a member of a binding pair to allow the capture of the primer on solid phase. In particular embodiments, the primers may be tagged with varying lengths of nonspecific polynucleotides (e.g., poly-GACT) to allow multiplex detection of preferably 2 or more, more preferably 3 or more, 4 or more, 5 or more, even 10 or more different mutations (polymorphisms) in a single reaction. The primer hybridizes to the PCR amplicon in the presence of one or more labeled ddNTPs and a DNA polymerase. The polymerase extends the primer by one nucleotide, adding a single, labeled ddNTP to the 3' end of the extension primer. The addition of a dideoxy nucleotide terminates chain elongation. If more than one dideoxynucleotide (e.g., ddATP, ddGTP, ddCTP, ddTTP, ddUTP, etc.) is used in a reaction, one or more can be labeled. If multiple labels are used, the labels can be distinguishable e.g., each is labeled with a different fluorescent colored dye. The products are labeled oligonucleotides, each one of which may be detected based on its label.

Suitable extension primers for several polymorphism genotypes are as follows:

TABLE 6

Extension primers for TPMT mutations

| Mutation | Primer Name | Primer Sequence |
|---|---|---|
| G238C Sense strand | 2AF Tag | 5'TTCACTTTTCAATCAACTTAAGTGTAA ATGTATGATTTTATGCAGGTTT-3' (SEQ ID NO: 18) |
| G238C Antisense strand | 2AR Tag | 5'CTTTTCATCAATAATCTTACCTTTAAC TACACTGTGTCCCCGGTCTG-3' (SEQ ID NO: 19) |
| G460A | 3A1F Tag | 5'TACACTTTAAACTTACTACACTAAAAT TTGACATGATTTGGGATAGAGGA-3' (SEQ ID NO: 20) |
| A719G | 3A2F Tag | 5'TACACTTTCTTTCTTTCTTTCTTTGGGA ATTGACTGTCTTTTTGAAAAGTTAT-3' (SEQ ID NO: 21) |

In preferred embodiments two different single nucleotide primer extension reactions are run: "the A reaction" and "the G reaction." The A reaction contains a labeled ddATP. For example, in this reaction, extension primers to detect the mutation at position 460 and the mutation at position 719 are used (e.g., SEQ ID NOs:20 and 21). Thus, when the nucleotide in position 460 is the mutant base (i.e. adenine), the label, indicating the presence of an adenine, will signal that the mutation is present. Conversely, when the base at position 719 is the wild-type base (i.e., adenine), incorporated label will indicate the presence of the wild type base at that position (see FIG. 2). The G reaction contains a labeled ddGTP. For example, in this reaction, extension primers to detect each of the mutations are used (e.g., SEQ ID NOs:18-21). Thus, when the base at position 238 is the wild-type base (i.e., guanine), incorporated label will indicate the presence of the wild type base at that position. Similarly, when the base at position 460 is the wild-type base (i.e., guanine), incorporated label will indicate the presence of the wild type base at that position. However, when the base at position 719 is the mutant base (i.e., guanine), incorporated label will indicate the presence of the wild type base at that position.

Detection of Labeled Extension Primers

Methods of detection of labeled extension primers are known in the art and vary depending on the nature of the label. In a preferred embodiment, extension primers are captured with labeled beads and detected using flow cytometry. Flow cytometry is a technique well-known in the art. Flow cytometers hydrodynamically focus a liquid suspension of particles (e.g., synthetic microparticles, microspheres, or beads) into an essentially single-file stream such that each particle can be analyzed individually. Flow cytometers are capable of measuring forward and side light scattering which correlates with the size of the particle and the particles may have their own label. Thus, particles of differing sizes may be used in invention methods simultaneously to detect distinct nucleic acid segments. In addition fluorescence at one or more wavelengths can be measured simultaneously. Consequently, particles can be sorted by size and/or fluorescence and the fluorescence of one or more associated fluorescently labeled probes can be analyzed. Exemplary flow cytometers include the Becton-Dickenson Immunocytometry Systems FACS-CAN.

In other embodiments the label is a fluorescent dye. Fluorescent dyes are detected through exposure of the label to a photon of energy of one wavelength, supplied by an external source such as an incandescent lamp or laser, causing the fluorophore to be transformed into an excited state. The fluorophore then emits the absorbed energy in a longer wavelength than the excitation wavelength which can be measured as fluorescence by standard instruments containing fluorescence detectors. Exemplary fluorescence instruments include spectrofluorometers and microplate readers, fluorescence microscopes, fluorescence scanners, and flow cytometers.

In addition to labeling nucleic acids with fluorescent dyes, the invention can be practiced using any apparatus or methods to detect detectable labels associated with nucleic acids of a sample, an individual member of the nucleic acids of a sample. Devices and methods for the detection of multiple fluorophores are well known in the art, see, e.g., U.S. Pat. Nos. 5,539,517; 6,049,380; 6,054,279; 6,055,325; and 6,294,331. Any known device or method, or variation thereof, can be used or adapted to practice the methods of the invention, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. Patent Application Nos. 20010018514; 20010007747; and published international patent applications Nos. WO0146467 A; WO9960163 A; WO0009650 A; WO0026412 A; WO0042222 A; WO0047600 A; and WO0101144 A.

Charge-coupled devices, or CCDs, are used in microarray scanning systems may be used in the practice of the methods of the invention. Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively, a spectral image can be made using brightfield microscopy, see, e.g., U.S. Pat. No. 6,294,331.

The following examples serve to illustrate the present invention. These examples are in no way intended to limit the scope of the invention.

EXAMPLE 1

Sample Preparation

Treatment of blood samples for direct PCR.

A) A 30 µL aliquot of a blood sample was combined with 90 µL of a solution containing 2% SDS, 50 mM Tris-HCl, pH 8.0, 10 mM EDTA. The resulting solution was diluted 1:125 in water prior to PCR amplification.

B) A 30 µL aliquot of a blood sample was combined with 90 µL of a solution containing 0.5M NaOAc, 0.2M Tris-HCl, 0.15M sodium ascorbate, 10 mM CDTA, 1% SDS, 30% (v/v) ethanol, pH 9.5 (see PCT International Publication No. WO03104251 at Table 3, lane 1). The mixture was incubated at 65° C. for approximately 30 minutes. 60 µL water was added and the solution mixed and centrifuged at 5000 rpm for 5 minutes. A 30 µL aliquot was pipetted off the top of the liquid and transferred to a fresh plate. This aliquot was diluted 1:25-1:125 prior to amplification by PCR.

C) A 30 µL aliquot of a blood sample was combined with 90 µL DNA preserving solution from the Oragene™ DNA Self-Collection Kit (DNA Genotek, Ottawa, Ontario, Canada was added. The mixture was incubated at 65° C. for approximately 30 minutes. 60 µL water was added and the solution mixed and centrifuged at 5000 rpm for 5 minutes. A 30 µL aliquot was pipetted off the top of the liquid and transferred to a fresh plate. This aliquot was diluted 1:25-1:125 prior to amplification by PCR.

EXAMPLE 2

Amplification of TPMT Fragments

Three regions of the TPMT gene, corresponding to each of the 3 TPMT mutations of interest (i.e., G238C, G460A, and A719G), are amplified by multiplex PCR.

A 5× solution of TPMT primer mix is prepared according to table 7 below.

TABLE 7

5× solution of TPMT primer mix

| Primer (50 µM) | Volume (µL) | Concentration 5X solution (µM) | Concentration Final solution (µM) |
|---|---|---|---|
| TPMT-E5F-linker (SEQ ID NO: 8) | 144 | 1.25 | 0.25 |
| TPMT-5R-linker (SEQ ID NO: 9) | 144 | 1.25 | 0.25 |
| TPMT-I6F-linker (SEQ ID NO: 10) | 230 | 2.00 | 0.40 |
| TPMT-I7R-linker (SEQ ID NO: 11) | 230 | 2.00 | 0.40 |
| TPMT-I9F-linker (SEQ ID NO: 12) | 173 | 1.50 | 0.30 |
| TPMT-R971-linker (SEQ ID NO: 13) | 173 | 1.50 | 0.30 |
| dH$_2$O | 4,666 | | |
| Total | 5,760 | | |

The TPMT PCR master mix is prepared according to table 8 below. This solution is stable for approximately 6 months at −70° C.

TABLE 8

TPMT PCR master mix

| Components | Per Rxn (µL) | x3000 (µL) |
|---|---|---|
| 10× Roche PCR Buffer | 2.5 | 7,500 |
| 25 mM dNTP mix | 0.25 | 750 |
| 5× TPMT primer mix | 5.0 | 15,000 |
| 25 mM MgCl$_2$ | 1.0 | 3,000 |
| Sterile H$_2$O | 14.0 | 42,000 |
| Total | 22.75 | 68,250 |

A 25 µL reaction containing 22.75 µL TPMT master mix, 0.25 µL Taq polymerase (HotStarTaq) and 2 µL of the genomic DNA-containing test sample or control DNA is run under the following PCR conditions.

TABLE 9

PCR amplification conditions

| Step | Temperature | Time |
|---|---|---|
| 1 | 95° C. | 15 min. |
| 2 | 94° C. | 30 sec |
| 3 | 60° C. | 60 sec. |
| 4 | 70° C. | 30 sec. |
| 5 | go to step 2 | 34 cycles* |
| 6 | 70° C. | 7 min. |
| 7 | 4° C. | Hold |

After PCR is complete, the samples are treated with SAP (shrimp alkaline phosphatase) and Exo I (exonuclease I). A fresh SAP/ExoI cocktail is prepared prior to each use according to table 10 below.

TABLE 10

SAP/ExoI cocktail

| Reagent | Volume (µL) for 1 reaction | Volume (µL) for 120 rxns (full plate) |
|---|---|---|
| SAP (1 unit/µL) | 7.5 | 900 |
| Exo I (10 unit/µL) | 0.3 | 36 |
| Sterile H$_2$O | 14.7 | 1,764 |
| Total | 22.5 | 2,700 |

22.5 µL of the SAP/ExoI cocktail is dispensed into each well of a 96-well plate. 7.5 µL of PCR product is added to each well. The samples are incubated at 37° C. for 2 hours, 75° C. for 15 minutes then chilled to 4° C. and stored at 2-8° C. until use.

EXAMPLE 3

Single Nucleotide Primer Extension

Two single nucleotide primer extension reactions (termed "the A reaction" and "the G reaction") are performed on the SAP/ExoI treated samples. The A reaction contains extension primers and labeled ddATP to allow the detection of mutation at position 460 (i.e., G460A) and the wild-type nucleotide at position 719. The G reaction contains extension primers and labeled ddGTP to allow the detection of mutation at position 238 of the antisense strand and the wild-type at position 238 of the sense strand. The G reaction further permits the detection of the wild-type nucleotide at position 460 and the mutation at position 460.

A Reaction

Prepare the primer extension (PE) primer master mix for the A reaction according to table 11 below.

TABLE 11

Primer Extension (PE) Primer Mix for A reaction

| Mutation | Primer | Concentration (µM) | Volume (µl) for 1 rxn | Volume (µl) for 4000 rxns |
|---|---|---|---|---|
| TPMT3B (G460A) | 3A1F Tag (SEQ ID NO: 20) | 100 uM | 0.1 | 400 |

TABLE 11-continued

Primer Extension (PE) Primer Mix for A reaction

| Mutation | Primer | Concentration (µM) | Volume (µl) for 1 rxn | Volume (µl) for 4000 rxns |
|---|---|---|---|---|
| TPMT3C (A719G) | 3A2F Tag (SEQ ID NO: 21) | 100 uM | 0.1 | 400 |
| H$_2$O | | | 0.2 | 800 |

The above extension primers are tagged with unique Tag-It DNA sequence™ (Luminex).

Prepare the biotin-ddATP/ddNTP mix for the A reaction according to table 12 below.

TABLE 12

Biotin-ddATP/ddNTP mix for A reaction

| Reagent | Concentration | Volume (µL) for 1 rxn | Volume (µL) for 120 rxns (full plate) |
|---|---|---|---|
| Biotin-ddATP | 1 mM | 0.1 | 12 |
| ddCTP | 1 mM | 0.5 | 60 |
| ddGTP | 1 mM | 0.5 | 60 |
| ddTTP | 1 mM | 0.1 | 12 |
| Total | | 1.2 | 144 |

The primer extension master mix for the A reaction is prepared according to table 13 below.

TABLE 13

Primer Extension Master Mix for A reaction

| Reagent | 1 Rxn (µL) | Full Plate 112 Rxns (µL) |
|---|---|---|
| 10× PCR Buffer(20 mM Mg++) | 2.0 | 224 |
| Biotin-ddATP/ddNTP mix | 1.2 | 134.4 |
| PE Primer Mix for A reaction | 0.4 | 44.8 |
| H$_2$O | 8.15 | 912.8 |
| Mixture Total | 11.75 | 1,316 |

7.5 µL of SAP/ExoI treated sample is added to 11.5 µL PE Master Mix for A Reaction and 0.75 µL Fast Start Taq (Roche). The thermal cycler conditions for the primer extension reaction are as follows:

TABLE 14

Primer extension reaction conditions

| Step | Temperature | Time |
|---|---|---|
| 1 | 96° C. | 2 min. |
| 2 | 95° C. | 30 sec |
| 3 | 50° C. | 30 sec |
| 4 | 60° C. | 30 sec |
| 5 | Go to Step 2 | 50 Cycles |
| 6 | 4° C. | 5 min |
| 7 | 4° C. | Hold |

G Reaction

The primer extension primer mix for the G reaction is prepared according to table 15 below.

TABLE 15

Primer extension (PE) primer mix for G reaction

| Mutation | Primer | Concentration (μM) | Volume (μL) for 1 rxn | Volume (μL) for 4000 rxns |
|---|---|---|---|---|
| TPMT*2 | 2F Tag (SEQ ID NO: 18) | 100 uM | 0.1 | 400 |
| TPMT*2 | 2R Tag (SEQ ID NO: 19) | 100 uM | 0.1 | 400 |
| TPMP*3B (460G > A) | 3A1F Tag (SEQ ID NO: 20) | 100 uM | 0.1 | 400 |
| TPMT*3C (719A > G) | 3A2F Tag (SEQ ID NO: 21) | 100 uM | 0.1 | 400 |
| H$_2$O | | | 0.4 | 1,600 |

The above extension primers are tagged with unique Tag-It DNA sequence™ (Luminex).

The Biotin-ddATP/ddNTP mix for G reaction is prepared according to table 16 below.

TABLE 16

Biotin-ddATP/ddNTP mix for G reaction

| Reagent | Concentration | Volume (μL) for 1 rxn | Volume (μL) for 120 rxns (full plate) |
|---|---|---|---|
| Biotin-ddGTP | 1 mM | 0.1 | 12 |
| ddCTP | 1 mM | 0.5 | 60 |
| ddATP | 1 mM | 0.5 | 60 |
| ddTTP | 1 mM | 0.1 | 12 |
| Total | | 1.2 | 144 |

The primer extension (PE) master mix for the G reaction is prepared according to table 17 below.

TABLE 17

Primer Extension Master Mix for G reaction

| Reagent | 1 Rxn (μL) | Full Plate 112 Rxns (μL) |
|---|---|---|
| 10× PCR Buffer(20 mM Mg++) | 2.0 | 224 |
| Biotin-ddGTP/ddNTP mix | 1.2 | 134.4 |
| PE Primer Mix for G reaction | 0.8 | 89.6 |
| H$_2$O | 7.75 | 868 |
| Mixture Total | 11.75 | 1,316 |

7.5 μL of SAP/ExoI treated sample is added to 11.5 μL PE Master Mix for G Reaction and 0.75 μL Fast Start Taq (Roche). The thermal cycler conditions for the primer extension reaction for the G reaction are the same as the conditions recited above for the A reaction.

EXAMPLE 4

Detection

The extension primers are captured on solid phase by hybridization of a the Tag-It DNA sequence to the corresponding Anti-Tag sequence (i.e., the complementary sequence to the tag sequence contained in the extension primer) coupled to the surface of a fluorescent-labeled microsphere. The microspheres are then subjected to flow cytometry in which the presence of labeled extension primer can be detected.

5× hybridization buffer is prepared according to table 18.

TABLE 18

5× hybridization buffer

| Regents | Concentration (M) | Volume (mL) or Weight (g) |
|---|---|---|
| Tris-HCl (pH 8.0) | 1M | 550 mL |
| Triton-100 | 100% | 4.4 mL |
| NaCl | | 64.25 g |
| H$_2$O | | ~440 mL* |

*The H$_2$O volume is an estimate, add H$_2$O last to the final volume of 1 L.

The Luminex 4 bead mix is prepared according to the following table. All beads are obtained from Luminex Corp. (Austin, Tex.). Each bead bottle is vortexed for 20 seconds followed by sonication for 20 seconds. Vortexing and sonication are repeated once more. The beads are light-sensitive and thus the bead solution needs to be kept away from light.

TABLE 19

Luminex 4 bead mix

| Bead Stock Solution 2.5 × 10$^5$/mL (Luminex FlexMAP microsphere) | Anti-Tag-it Sequence | 1 Reaction (μL) | Full Plate (112 Reactions) (μL) |
|---|---|---|---|
| 031 (Cat. No. L-100-031) | 5'AGTTGATTGAAAAGT GAA-3' (SEQ ID NO: 22) | 9 | 1,000 |
| 065 (Cat. No. L-100-065) | 5'AAAGGTAAGATTATT GATGAAAAG-3' (SEQ ID NO: 23) | 9 | 1,000 |
| 095 (Cat. No. L-100-095) | 5'TTAGTGTAGTAAGTTT AAAGTGTA-3' (SEQ ID NO: 24) | 9 | 1,000 |
| 012 (Cat. No. L-100-012) | 5'AAAGAAAGAAAGAA AGAAAGTGTA-3' (SEQ ID NO: 25) | 9 | 1,000 |
| ddH2O | | 4 | 480 |
| Total | | 40 | 4,480 |

The bead hybridization is performed as follows. A bead hybridization solution is prepared according to the following table.

TABLE 20

Bead hybridization solution

| Reagent | 1 Reaction (μL) | Full Plate (112 Reactions) (μL) |
|---|---|---|
| 4 Bead Mix | 40 | 4,480 |
| 5× Hyb. Buffer | 10 | 1,120 |
| Total | 50 | 5,600 |

50 μL of the bead hybridization solution is added to each appropriate well of an ABI Optical 96-well plate. 5 μL of the Primer Extension product (from Example 3) is added. The plate is sealed but not vortexed or centrifuged. Centrifugation of the bead hybridization plate will cause the beads to form a pellet at the bottom of the plate and not hybridize to the primer extension product. The plate is placed in a thermal cycler and subjected to table 21 below.

TABLE 21

Bead hybridization conditions

| Step | Temp. | Time |
|---|---|---|
| 1 | 96° C. | 2 min. |
| 2 | 37° C. | 1 hour |
| 3 | 37° C. | Hold |

The wash solution is prepared according to table 22.

TABLE 22

Wash solution (1× Hybridization buffer)

| Reagent | 1 Rxn (μL) | 112 Rxn Full Plate (μL) |
|---|---|---|
| ddH2O | 120 | 13,440 |
| 5× Hyb. Buffer | 30 | 3,360 |
| Total | 150 | 16,800 |

Prepare the reporter solution of streptavidin R-phycoerythrin (SA-PE) conjugate by vortexing the tube of SA-PE for 2-5 seconds. Add appropriate amount of SA-PE to appropriate 1× hybridization buffer. SA-PE is light sensitive so exposure to light should be limited and the solution stored in the dark until ready to use. Prepare 5-10 minutes before use.

TABLE 23

Reporter solution

| Loading Mix | 1 Rxn (μL) | Full Plate x112 Rxn |
|---|---|---|
| 1× Hybridization Buffer | 150 | 16800 |
| SA-PE | 0.4 | 44.8 |
| Total | 150.4 | 16,844.8 |

The bead hybridization plate is removed from the thermal cycler. The plate is sealed and spun at 3000 RCF (not rpm) for 5 minutes in a microplate centrifuge. The plate is inverted over paper towels and tapped to remove excess liquid. 150 μL of wash solution is added to each well. The plate is sealed and vortexed for 10 seconds. Vortexing is repeated two more times. The plate is sealed and spun at 3000 RCF (not rpm) for 5 minutes in a microplate centrifuge. The plate is inverted over paper towels and tapped to remove excess liquid. 150 μL of reporter solution is added to each well. The 150 μL solution is carefully pipetted up and down 8 times. The solution is transferred to a new Falcon DB 96-well plate. The plate is placed in the dark for 15 minutes then placed on the Luminex 100 IS instrument. The results of the detection by the Luminex 100 IS instrument are correlated to the genotype at each mutation position as follows.

TABLE 24

Detection results for the A Reaction

| Primer | ΔMFI* | Wild-type (Wt) or mutation | Genotypes |
|---|---|---|---|
| 3A1F Tag | >400 | Mutation | 460A |
| 3A2F Tag | >800 | Wt | 719A |

*ΔMFI is the MFI of samples with DNA minus the MFI of samples without DNA control.

TABLE 25

Detection results for the G Reaction

| Primer | ΔMFI* | Wild-type (Wt) or mutation | Genotypes |
|---|---|---|---|
| 2AF Tag | >800 | Wt | 238G |
| 2AR Tag | >800 | Mutation | 238C |
| 3A1F Tag | >800 | Wt | 460G |
| 3A2F Tag | >800 | Mutation | 719G |

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

---

That which is claimed is:

1. A method for determining the presence or absence of mutations in a Thiopurine S-methyltransferase (TPMT) gene comprising SEQ ID NO: 1 from a nucleic acid sample from a person, said method comprising:
   a) amplifying one or more regions of the TPMT gene to create one or more amplified regions;
   b) performing three single nucleotide primer extensions using at least three extension primers to detect the identity of the nucleotide added to each of the extension primers in two reactions, wherein each reaction contains only a single labeled ddNTP, wherein the identity of the nucleotide indicates the presence of absence of a mutation in the TPMT gene, and wherein the first reaction comprises labeled ddATP to detect the presence of the G460A mutation and the absence of the A719G mutation and the second reaction comprises labeled ddGTP to detect the absence of the G238C mutation.

2. The method of claim 1, wherein said amplifying is accomplished with polymerase chain reaction.

3. A method according to claim 1, wherein at least one said extension primer includes a tag.

4. A method according to claim 3, wherein said tag comprises an oligonucleotide.

5. A method according to claim 4, wherein step b) further comprises capturing at least one extension primer products on beads, wherein said beads comprise an oligonucleotide complementary to the oligonucleotide tag on the extension primer, by hybridization of said complementary oligonucleotide with the oligonucleotide tag, and wherein said detecting further comprises detecting labeled captured extension primers by subjecting the beads to flow cytometry.

6. The method of claim 1, wherein said labeled ddATP and ddGTP are fluorescently labeled.

7. The method of claim 1, wherein said single nucleotide extension primers are selected from the group consisting of SEQ ID NOs:18-21.

8. A method according to claim 1 wherein step a) comprises amplifying three regions of the TPMT gene.

9. A method according to claim 1, wherein the regions are amplified in the same vessel.

10. A method according to claim 1, wherein the second reaction further comprises primers to detect the presence of the A719G mutation and/or the absence of the G460A mutation.

11. A method according to claim 10, wherein said extension primers of said second reaction includes SEQ ID NOs:18 and/or 19.

12. A method according to claim 1, wherein said extension primers of said first reaction includes each of SEQ ID NO:20 and SEQ ID NO:21.

13. The method of claim 1, wherein the method further comprises contacting the sample with a nucleic acid processing solution (NAPS) having a chelating agent, a denaturing agent, and a buffering agent to form a modified sample, wherein the NAPS has a pH between about 5 and about 11, and using the modified sample as a template in step a).

14. A method according to claim 13, wherein said pH is between about 7 and about 10.

15. The method according to claim 13, wherein said chelating agent is selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), desferrioximine, and analogs thereof.

16. A method according to claim 13, wherein said denaturing agent is selected from the group consisting of: urea, sodium dodecyl sulfate, dodecyl sulfate, guanidinium chloride, guanidinium thiocyanate, perchlorate, methanol, ethanol, n-propanol, isopropanol, n-butanol, trifluoroethanol, phenol, and 2,6-di-tert-butyl-4-methylphenol.

17. A method according to claim 13, wherein said sample is whole blood.

18. A method according to claim 1, wherein said sample is whole blood.

19. A method of identifying an individual who is susceptible to toxicity of thiopurine drugs due to reduced activity of Thiopurine S-methyltransferase (TPMT) by determining the presence or absence of mutations in the TPMT gene comprising SEQ ID NO: 1 from a nucleic acid sample from an individual, said method comprising,
    a) amplifying one or more regions of the TPMT gene to create one or more amplified regions;
    b) performing three single nucleotide primer extensions using at least three extension primers to detect the identity of the nucleotide added to each of the extension primers in two reactions, wherein each reaction contains only a single labeled ddNTP, wherein the identity of the nucleotide indicates the presence or absence of a mutation in the TPMT gene, wherein the first reaction comprises labeled ddATP to detect the presence of the G460A mutation and the absence of the A719G mutation and the second reaction comprises labeled ddGTP to detect the absence of the G238C mutation; and
    c) identifying the individual as being susceptible to toxicity of thiopurine drugs when a mutation identified in step b) is present.

20. The method of claim 19, wherein said amplifying is accomplished with polymerase chain reaction.

21. A method according to claim 19, wherein at least one said extension primer includes a tag.

22. A method according to claim 21, wherein said tag comprises an oligonucleotide.

23. A method according to claim 22, wherein step b) further comprises capturing at least one extension primer product on beads, wherein said beads comprise an oligonucleotide complementary to the oligonucleotide tag on the extension primer, by hybridization of said complementary oligonucleotide with the oligonucleotide tag, and wherein said detecting further comprises detecting labeled captured extension primers by subjecting the beads to flow cytometry.

24. The method of claim 19, wherein said labeled ddATP and ddGTP are fluorescently labeled.

25. The method of claim 19, wherein said single nucleotide extension primers are selected from the group consisting of SEQ ID NOs:18-21.

26. A method according to claim 19, wherein step a) comprises amplifying three regions of the TPMT gene.

27. A method according to claim 19, wherein the regions are amplified in the same vessel.

28. A method according to claim 19, wherein the second reaction further comprises primers to detect the presence of the A719G mutation or the absence of the G460A mutation.

29. A method according to claim 28, wherein said extension primers of said second reaction includes SEQ ID NOs: 18 and/or 19.

30. A method according to claim 19, wherein said extension primers of said first reaction includes each of SEQ ID NO: 20 and SEQ ID NO: 21.

* * * * *

SEQUENCE LISTING

<160> NUMBER OF SEQ ID NOS: 25

<210> SEQ ID NO 1
<211> LENGTH: 738
<212> TYPE: DNA
<213> ORGANISM: Homo sapiens

<400> SEQUENCE: 1

```
atggatggta caagaacttc acttgacatt gaagagtact cggatactga ggtacagaaa      60
aaccaagtac taactctgga agaatggcaa gacaagtggg tgaacggcaa gactgctttt     120
catcaggaac aaggacatca gctattaaag aagcatttag atactttcct taaaggcaag     180
agtggactga gggtattttt tcctctttgc ggaaaagcgg ttgagatgaa atggtttgca     240
gaccggggac acagtgtagt tggtgtggaa atcagtgaac ttgggataca agaattttt      300
acagagcaga atctttctta ctcagaagaa ccaatcaccg aaattcctgg aaccaaagtw     360
tttaagagtt cttcggggaa catttcattg tactgttgca gtattttga tcttcccagg      420
acaaatattg gcaaatttga catgatttgg gatagaggag cattagttgc cattaatcca     480
ggtgatcgca aatgctatgc agatacaatg ttttccctcc tgggaaagaa gtttcagtat     540
ctcctgtgtg ttctttctta tgatccaact aaacatccag gtccaccatt ttatgttcca     600
catgctgaaa ttgaaaggtt gtttggtaaa atatgcaata tacgttgtct tgagaaggtt     660
gatgcttttg aagaacgaca taaaagttgg ggaattgact gtcttttga aaagttatat      720
ctacttacag aaaagtaa                                                    738
```

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctttgaaac cctatgaacc tg                                                22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taggaaccat cggacacatg                                                   20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

-continued ctccacaccc aggtccacac att                                               23

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtatagtata ctaaaaaatt aagacagcta aac                                    33

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatccctgat gtcattcttc atagtattt                                         29

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catccattac attttcaggc tttagcataa t                                      31

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggtcccaa aagggtcagt tgtctttgaa accctatgaa cctg                        44

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggtcccaa aagggtcagt tgtaggaacc atcggacaca tg                          42

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggtcccaa aagggtcagt tgctccacac ccaggtccac acatt                       45

-continued

```
<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggtcccaa aagggtcagt tggtatagta tactaaaaaa ttaagacagc taaac            55

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggtcccaa aagggtcagt tgaatccctg atgtcattct tcatagtatt t                51

<210> SEQ ID NO 13
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggtcccaa aagggtcagt tgcatccatt acattttcag gctttagcat aat              53

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taagtgtaaa tgtatgattt tatgcaggtt t                                      31

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aactacactg tgtccccggt ctg                                               23

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatttgacat gatttgggat agagga                                            26
```

```
<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggaattgac tgtcttttg aaaagttat                                          29

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18 ttcactttc aatcaactta agtgtaaatg tatgatttta tgcaggttt                    49

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttttcatca ataatcttac ctttaactac actgtgtccc cggtctg                     47

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tacactttaa acttactaca ctaaaatttg acatgatttg ggatagagga                  50

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tacactttct ttctttcttt ctttgggaat tgactgtctt tttgaaaagt tat              53

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agttgattga aaagtgaa                                                     18
```

-continued

```
<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaggtaaga ttattgatga aaag                                          24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttagtgtagt aagtttaaag tgta                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaagaaagaa agaaagaaag tgta                                          24
```